United States Patent [19]  [11] 4,124,452
Henderson  [45] Nov. 7, 1978

[54] DISTILLATION TECHNIQUE FOR REMOVAL OF UDMH FROM WATER

[75] Inventor: Larry D. Henderson, Bryans Road, Md.

[73] Assignee: The United States of America as represented by the Secretary of the Navy, Washington, D.C.

[21] Appl. No.: 908,321

[22] Filed: May 22, 1978

[51] Int. Cl.$^2$ .................. B01D 3/40; C07C 85/26; C07C 87/24

[52] U.S. Cl. .................. 203/56; 203/51; 203/63; 203/37; 260/583 B

[58] Field of Search .................. 203/37, 51, 56, 57, 203/63, 70; 260/583 B

[56] References Cited

U.S. PATENT DOCUMENTS

| | | |
|---|---|---|
| 2,698,286 | 12/1954 | Bircher, Jr. .................. 203/63 X |
| 2,799,631 | 7/1957 | Von Hessert .................. 203/37 |
| 2,858,254 | 10/1958 | Nicolaisen et al. .................. 260/583 B X |
| 2,876,173 | 3/1959 | Nicolaisen .................. 260/583 B X |
| 2,963,407 | 12/1960 | Lewis .................. 203/63 X |
| 3,098,017 | 7/1963 | Walter, Jr. et al. .................. 260/583 B X |
| 3,102,144 | 8/1963 | Horvitz .................. 260/583 B |
| 3,274,251 | 9/1966 | Besson et al. .................. 260/583 B |
| 4,046,812 | 9/1977 | Langer et al. .................. 260/583 B |

FOREIGN PATENT DOCUMENTS

| | | |
|---|---|---|
| 654,797 | 12/1962 | Canada .................. 260/583 B |
| 92,791 | 2/1962 | Denmark .................. 260/583 B |

*Primary Examiner*—Morris O. Wolk
*Assistant Examiner*—Michael S. Marcus
*Attorney, Agent, or Firm*—R. S. Sciascia; A. L. Branning; H. B. Field

[57] ABSTRACT

A process for extracting essentially pure unsymmetrical dimethyl hydrazine (UDMH) from a solution containing UDMH, water, and other volatiles and non-volatiles, comprises charging a distillation stillpot with the UDMH solution, mixing into the solution sufficient caustic sodium hydroxide so as to cause the solution to separate into a two layer system, mixing isopropanol into the two layer system, and distilling off the essentially pure UDMH distillate.

6 Claims, No Drawings

DISTILLATION TECHNIQUE FOR REMOVAL OF UDMH FROM WATER

BACKGROUND OF THE INVENTION

This invention relates to a process for recovering unsymmetrical dimethyl hydrazine (UDMH). More specifically, pure UDMH is recovered from a solution of UDMH, water, and other volatiles and non-volatiles by adding a distillation agent to the solution.

It is important to note that the three amine fuels, UDMH, monomethylhydrazine, and anhydrous hydrazine are each very dissimiliar materials. The hydrazines are so named because of the nitrogen bonding within the molecule. The differences between the three hydrazines are attributable primarily to either the absence of or presence of one or two carbon atoms with bonds to adjacent hydrogen atoms. Unsymmetrical dimethyl hydrazine does not form an azeotrope with water while both of the other materials do form these azeotropes. There are numerous techniques available for dehydration of the azeotrope called hydrazine hydrate. U.S. Pat. Nos. 2,963,407 and 2,698,286 teach these techniques. In one case various alcohols are added to break the azeotrope form by allowing water to migrate up to the top of the column from where it can be removed as overhead product. In the other case, materials such as analine are used in order to break the azeotrope. The difference between the dehydration techniques employed for anhydrous hydrazine and monomethylhydrazine are slight even though the major difference between these materials is that in one case for hydrazine there is a purely inorganic compound, while in the case of monomethylhydrazine there are carbon and hydrogen atoms involved within the molecule. In the case of separation by addition of a alcohol, the water is removed from the azeotrope by taking it up the column and removing water/alcohol as a product. This situation does not occur in the case of UDMH. The isopropanol treated within the present invention is utilized as a means for isolation between the water and UDMH thereby keeping both the water and the isopropanol in the distillation pot. Since unsymmetrical dimethyl hydrazine does not form an azeotrope but only has an affinity for water (as evidenced by a pinch point at the low concentrations of UDMH in water) it is necessary to treat UDMH differently as it really behaves differently than the other hydrazines. The use of isopropanol in U.S. Pat. No. 2,936,407 is only in the case where the alcohol passes up the column, thus the alcohol serves an entirely different function within this invention.

Should an experimentor investigate the boiling points of UDMH water and isopropanol, he would find that isopropanol has a boiling point midway between the low boiling unsymmetrical dimethyl hydrazine and the higher boiling water. He would have found that this is not the case with respect to the materials treated in the aforementioned patents and would not have applied isopropanol within this context to the separation of UDMH and water.

SUMMARY OF THE INVENTION

Accordingly, there is provided by the present invention a process for extracting essentially pure UDMH from a solution containing UDMH, water, and other volatiles and non-volatiles, comprises charging a distillation stillpot with a UDMH solution, mixing into the UDMH solution sufficient caustic sodium hydroxide to cause the UDMH solution to separate into a two layer system, then mixing into the two layer system isopropanol in an amount ranging from about 1 to about 5 weight percent of the solution, and distilling the isopropanol ladened two layer system so as to generate an essentially pure UDMH distillate.

OBJECTS OF THE INVENTION

Therefore, it is an object of the present invention to provide a means for extracting pure UDMH from a solution containing UDMH, water, and other volatiles and non-volatiles.

Another object of the present invention is to keep the temperature of the distillation stillpot as low as possible.

Yet another object of the present invention is to allow the UDMH to be extracted from the caustic phase of a two phase system.

Still another object of the present invention is to reduce the amount of UDMH decomposition during distillation.

Yet another object of the present invention is to eliminate water in the UDMH distillate.

Other objects, advantages, and novel features of the present invention will become apparent from the following detailed description of the invention.

DESCRIPTION OF THE PREFERRED EMBODIMENTS

UDMH manufacturing techniques currently employed yield a product which comprises UDMH, water, ammonia, dimethylamine and other volatiles and non-volatiles. However, techniques used todate to extract the pure UDMH from the product solution have had many drawbacks. Now, essentially pure UDMH can efficiently be recovered from the UDMH product solution by the addition of a distillation agent.

In general, the process for extracting essentially pure unsymmetrical dimethyl hydrazine from a solution containing UDMH, water, and other volatiles and non-volatiles comprises charging a distillation stillpot with the UDMH solution, mixing into the solution sufficient caustic sodium hydroxide so as to cause the solution to separate into a two layer system, mixing a distillation agent such as isopropanol, hexane, or ethanol into the two layer system, and distilling off the essentially pure UDMH distillate.

More specifically, a UDMH solution is charged into a distillation stillpot. To the UDMH solution sufficient caustic sodium hydroxide is added to cause the solution to separate into a two layer system. The bottom layer of this system should have from about 10 to about 50 weight percent sodium hydroxide with the preferred amount being about 30 weight percent. This can be measured in any conventional manner however, one simple method would be by measuring the specific gravity of the bottom layer at 120° F. Thus, the specific gravity of a 10 weight percent caustic solution would be about 1.09, the specific gravity of the preferred 30 weight percent caustic solution would be about 1.32, and the specific gravity of a 50 weight percent solution would be about 1.52. The use of caustic is described in more detail in U.S. Pat. No. 2,876,173 to Nicolaisen included herein by reference.

Once the above two layer system has been prepared, a distillation agent is mixed into the system. The distillation agent can be any nonreactive organic solvent whose boiling point lies between UDMH and water. Preferred distillation agents include hexane, isopropanal and ethanol, while the most preferred distillation agent is isopropanol. Based upon the weight of the UDMH solution originally charged into the distillation stillpot, from about 1 to about 5 weight percent of the distillation agent is mixed into the two layer system. The preferred amount of distillation agent is about 3 weight percent. Once the distillation agent has been thoroughly admixed with the two layer system the distillation process can be initiated.

The addition of the distillation agent to the two layer system yields a number of previously unobtainable advantages. First, the stillpot temperature can easily be maintained between 188° F. (86° C.) and 200° F. (93° C.) thereby significantly decreasing the amount of UDMH which previously would decompose during distillation. Secondly, as the distillation occurs with greater purity when isopropanol is present, the reflux ratio (the amount of UDMH returned to the top of the distillation column as a ratio to the quantity of material removed from the processes product) may be decreased thereby concerving both time and energy in the manufacture of the final UDMH product. Thirdly, water is eliminated from the final UDMH product because the distillation endpoint is clearly marked by the occurrence of a significant temperature increase midway up the distillation column and by the distillation agent serving as a barrier. Finally, the concentration of UDMH remaining in the stillpot can be reduced to less than 1 weight percent without water carryover.

By way of example and not limitation the following process is described. A twelve thousand gallon batch of UDMH solution containing ammonia, dimethylamine, UDMH, water, and other volatiles and non-volatiles was charged into a distillation stillpot. Then sufficient caustic was mixed into the UDMH solution to bring the forming bottom layer to approximately 32 weight percent sodium hydroxide. Approximately 500 gallons of isopropanol was then mixed into the two layer system. Upon distillation in a 32 tray distillation column, the pot temperature remained at between about 190° F. and about 195° F. and the reflux ratio was kept at about 1.3:1. The end of distillation of the essentially pure UDMH was clearly indicated when the pot temperature rose rapidly to about 210° F. (99° C.).

Obviously, many modifications and variations of the present invention are possible in light of the above teachings. It is therefore to be understood that, within the scope of the appended claims, the invention may be practiced otherwise than as specifically described.

What is new and desired to be secured by Letters Patent of the United States is:

1. A process for extracting essentially pure unsymmetrical dimethyl hydrazine from a solution containing unsymmetrical dimethyl hydrazine, water, and other volatiles and non-volatiles, comprises:

charging a stillpot with a solution containing unsymmetrical dimethylhydrazine, water, and other volatiles and non-volatiles;

mixing into said solution sufficient caustic sodium hydroxide to cause said solution to separate into a two layer system;

mixing into said two layer system a distillation agent selected from the group consisting of hexane, ethanol and isopropanol, in an amount ranging from about 1 to about 5 weight percent of said solution; and distilling said two layer system so as to generate an essentially pure unsymmetrical dimethyl hydrazine distillate.

2. The process of claim 1 wherein said caustic varies from about 10 to about 50 weight percent of the bottom layer of said two layer system.

3. The process of claim 2 wherein said caustic is about 30 weight percent of the bottom layer of said two layer system.

4. The process of claim 1 wherein said distillation agent is isopropanol.

5. The process of claim 1 wherein said distillation agent is about 3 weight percent of said solution.

6. The process of claim 1 wherein said distillation is conducted between about 188° F. (86° C.) and 200° F. (93° C.).

* * * * *